US012653907B2

(12) United States Patent
Parrish

(10) Patent No.: US 12,653,907 B2
(45) Date of Patent: *Jun. 16, 2026

(54) METHODS OF TREATING OR PREVENTING AGE-RELATED DISORDERS

(71) Applicant: BioViva USA, Inc., Bainbridge, WA (US)

(72) Inventor: Elizabeth Louise Parrish, Bainbridge, WA (US)

(73) Assignee: BioViva USA, Inc., Bainbridge, WA (US)

( * ) Notice: Subject to any disclaimer, the term of this patent is extended or adjusted under 35 U.S.C. 154(b) by 1116 days.

This patent is subject to a terminal disclaimer.

(21) Appl. No.: 17/585,783

(22) Filed: Jan. 27, 2022

(65) Prior Publication Data

US 2022/0143218 A1 May 12, 2022

Related U.S. Application Data

(63) Continuation-in-part of application No. 15/369,783, filed on Dec. 5, 2016, now Pat. No. 11,266,721.

(60) Provisional application No. 62/325,158, filed on Apr. 20, 2016.

(51) Int. Cl.
| | |
|---|---|
| *A61K 48/00* | (2006.01) |
| *A61P 3/08* | (2006.01) |
| *A61P 21/00* | (2006.01) |

(52) U.S. Cl.
CPC .............. *A61K 48/005* (2013.01); *A61P 3/08* (2018.01); *A61P 21/00* (2018.01)

(58) Field of Classification Search
None
See application file for complete search history.

(56) References Cited

U.S. PATENT DOCUMENTS 11,266,721 B1    3/2022  Parrish

FOREIGN PATENT DOCUMENTS

| | | |
|---|---|---|
| EP | 2402038 B1 | 5/2016 |
| WO | 2012/001170 A1 | 1/2012 |

OTHER PUBLICATIONS

Kota et al., ScienceTranslationMedicine.org Nov. 11, 2009 vol. 1 issue 6 6ra15, pp. 1-8 (Year: 2009).*
Zaidy et al.,Journal of Neuromuscular Diseases 2 (2015) 185-192 (Year: 2015).*
Zhao et al., Molecular Therapy, vol. 23, No. 5, pp. 866-874, May 2015 (Year: 2015).*
Aoyagi et al.; Cancer cachexia, mechanism and treatment; World J Gastrointest Oncol Apr. 15, 2015; 7(4): 17-29 (Year: 2015).
Bernardes de Jesus et al.; Telomerase gene therapy in adult and old mice delays aging and increases longevity without increasing cancer; EMBO Molecular Medicine, vol. 4, No. 8, Aug. 1, 2012, pp. 691-704 (Year: 2012).
Callaway; Telomerase reverses ageing process; Nature News; published Nov. 28, 2010, pp. 1-3 (Year: 2010).
De Magalhaes et al.; Telomeres and Telomerase: A Modern Fountain of Youth ?; Rejuvenation Research; vol. 7, No. 2, 2004, pp. 126-133 (Year: 2004).
Manix et al.; Creutzfeldt-Jakob disease: updated diagnostic criteria, treatment algorithm, and the utility of brain biopsy; Neurosurgical Focus, vol. 39, E2, pp. 1-11, Nov. 2015 (Year: 2015).
Vickers; A vaccine against Alzheimer's disease: developments to date. Drugs Aging 2002; 19(7):487-94 (Year: 2002).

* cited by examiner

*Primary Examiner* — Evelyn Y Pyla
(74) *Attorney, Agent, or Firm* — Workman Nydegger

(57) ABSTRACT

Disclosed are methods for reducing effects of aging in a subject by administering a therapeutically effective amount of a human Telomerase Reverse Transcriptase (hTERT) gene in combination with a Follistatin-344 gene. The subject may be a human. The methods can beneficially increase telomere length in the treated subject.

14 Claims, 5 Drawing Sheets

Specification includes a Sequence Listing.

July 2021

Test (Date)

Chronological Age (years)

METHODS OF TREATING OR PREVENTING AGE-RELATED DISORDERS

CROSS-REFERENCE TO RELATED APPLICATIONS

This application is a continuation-in-part of U.S. patent application Ser. No. 15/369,783 filed on Dec. 5, 2016, which claims benefit of Provisional Appl. No. 62/325,158 filed on Apr. 20, 2016, the contents of which are incorporated herein in their entirety by reference.

INCORPORATION BY REFERENCE OF SEQUENCE LISTING

This application includes a Sequence Listing submitted electronically in ASCII format. The ASCII copy of the Sequence Listing, created on Jan. 19, 2022, is named 22425-2-1-1-SL.txt and is 2,931 bytes in size. The ASCII copy of the Sequence Listing is expressly incorporated herein by this reference.

BACKGROUND

Technical Field

This disclosure relates to the field of gene therapy, specifically to the field of treating or preventing age-related disorders with cost effective gene therapy.

Related Technology

Progress in the study of genetics and cellular biology over the past three decades has greatly enhanced our ability to describe the molecular basis of many human diseases and conditions. For example, as humans and other organisms age, many biological functions and machinery begin to break down and become less efficient.

SUMMARY

TERT Gene

Telomerase is a ribonucleoprotein that catalyzes the addition of telomeric repeats to the ends of telomeres. Telomeres are long stretches of repeated sequences that cap the ends of chromosomes. In humans, telomeres are typically 7-10 kilobase pairs (kb) in length and comprise multiple repeats, though human telomeres can get as low as about 3 to 5 kb and as high as about 12 kb. Telomerase is not expressed in most adult cells, and telomere length decreases with successive rounds of replication.

Telomerase acts as reverse transcriptase in the elongation of telomeres, which prevent the loss of telomeres due to the replication process. Without telomerase, the telomeres are shortened at each cell division which leads to senescence, apoptosis and cell death caused by chromosome instability. Telomerase is inactive in somatic cells but active in 90% of cancer cells, where telomerase is reactivated. Although telomerase activation may be dangerous, because it can mimic the cancer development process, telomerase enhancing agents may be theoretically applicable as anti-aging agents and clinically useful in certain medical conditions. In contrast, telomerase inhibitors may be useful to fight cancer. Cancer and aging are closely inter-related: interventions that protect against cancer can lead to premature aging while immortalization of cells is required in the formation of malignant cancer cells. Despite the theoretical risk of activation of carcinogenesis, activation of telomerase may lead to reduced rate of aging.

Lack of telomerase activity and/or expression and short telomeres may cause dyskeratosis congenita, aplastic anemia, increased risk of death due to cardiovascular diseases, strokes or infections, hypertension, or chronic stress. It was shown that transduction of telomerase in telomerase-knockout mice prevented damage in the liver. In addition to the role of telomerase in telomere length maintenance, accumulating data suggests that the telomerase reverse transcriptase (TERT) protein has additional physiological functions, i.e., protecting cells in mice from various damages in a mechanism (yet unclear) that does not involve telomere elongation.

Decades of work with telomerase and telomeres prove that such technology can be successfully used to regenerate aging cells and tissues, and to rejuvenate the human body, restoring it to a level similar to youthful function. Since shortly before the turn of the century, there has been ongoing research into the potential of interventions in telomerase in regenerative medicine. In 1999, scientists at Geron Corporation demonstrated that, through the use of telomerase activation, the aged cell could not only reset its Hayflick limit but could revert its gene expression to an earlier point in its life cycle. Shelton, Dawne et al., Current Biology 9,17 (1999): 939-945, incorporated herein in its entirety by reference. After 2000, evidence continues to mount that the restoration of telomeres in fact convey stability of gene expression, youthful function and a level of protection against cancer. The stable gene expression seen during youth may likely account for the rarity of cancer and resistance to disease and dysfunction enjoyed during youth.

Age reversal has been seen in fibroblasts and keratinocytes of the elderly. With the telomere length in fibroblast and keratinocyte cells reset to that a profile reflecting younger skin, the cells actually express the phenotype of the profile reflecting younger skin. Telomerase activation can reverse the age of a cell to a youthful state not only in appearance but also in terms of function and gene expression. Funk, Walter D et al., Experimental Cell Research 258.2 (2000): 270-278, incorporated herein in its entirety by reference. Similar results have been demonstrated with human vascular cells, Matsushita, Hidetsugu et al., Circulation Research 89.9 (2001): 793-798. , elderly osteoclasts (bone cells). Yudoh, Kazuo et al., Journal of Bone and Mineral Research 16.8 (2001): 1453-1464. The conclusion is that telomerase activation extends the telomeres and leads to a return of youthfulness in all cell types. In the early $21^{st}$ century, Ronald DePhinho published studies on the inhibitory effect of telomerase on telomere loss in the aging cell. Sahin, ErgUn, and Ronald A DePinho, Nature 464.7288 (2010): 520-528, Jaskelioff, Mariela et al., Nature 469.7328 (2011): 102-106, Sahin, ErgUn, and Ronald A DePinho. Nature revjews Molecular cell biology 13.6 (2012): 397-404, Sahin, ErgUn et al., Nature 470.7334 (2011): 359-365. The foregoing are incorporated herein in their entireties by reference.

Unfortunate, and unfounded, concerns that telomerase might promote neoplastic change chilled the development of its potential during the 1990's. These concerns were not shown to be unfounded until 2011, in the explanations published by Wright and Shay. Shay, Jerry W, and Wright, Woodring E., Seminars in Cancer Biology, 31 Dec. 2011: 349-353; Harley, Calvin B., Oncogene 21.4 (2002): 494-502; and Blasco. Marfa A., et al., Cell 91.1 (1997): 25-34; de Jesus, Bruno Bernardes, and Blasco, Maria A., Trends in Genetics 29.9 (2013): 513-520. Experiments showed that immune function in particular can show significant improvement with the use of weak telomerase activators as part of a health regimen. Harley, Calvin et al., Rejuvenation research 14.1(2011): 45-56. In 2012, Maria Blasco demonstrated that cellular age could be reversed by the delivery of telomerase via an adeno-associated viral (AAV) vector (de Jesus, Bruno Bernardes et al., EMBO Molecular Medicine 4.8 (2012): 691-704) and created a model for demonstrating the regenerative potential of telomerase and the resetting of cellular telomeres, Bar, Christian et al. Nature Communications 5 (2014). Blasco further reviews some of the multiple potential methodologies of the administration of telomerase as an anti-aging therapy. de Jesus, Bruno Bernardes, and Maria A Blasco., Current Opinion in Cell Biology 24.6 (2012): 739-743. The foregoing are incorporated herein in their entireties by reference.

Comparison of gene expression in youthful, elderly, and TERT-treated human cells demonstrates that eighty-four percent of the initially up-regulated and eighty-six percent of the down-regulated genes showed at least a 1.2-fold reversion to youthful profiles. Lackner, Daniel H et al. Aging Cell 13.5 (2014): 946-950, incorporated herein in its entirety by reference. While expression was not completely restored in all cases, only a few genes failed to show any reversion. Importantly, in cells that had reserves of telomeres, the activation of TERT had no effect on gene expression, showing that there is a natural optimum point of telomere extension. This paves the way for development of further telomerase therapeutics and may lead to full body organ rejuvenation and restoration of youthful gene expression.

Stem-cell niches are areas of a tissue that provide a specific microenvironment, in which stem cells are present in an undifferentiated and self-renewable state. Cells of the stem-cell niche interact with stem cells to maintain them or promote their differentiation. Mobilization or differentiation of stem cells in their niches is a key process in organ homeostasis and continued function. Maria Blasco has demonstrated that telomerase activity is linked to mobilization of stem cells, specifically in the dermis though likely a universal mechanism. Flores, Ignacio, Maria L Cayuela, and Maria A Blasco., Science 309.5738 (2005): 1253-1256, incorporated herein in its entirety by reference. The loss of telomeres inhibited stem cell mobilization from the niche leading to impairment of hair growth and skin cell proliferation, but TERT expression promotes cell mobilization independent of telomere length. This demonstrates an additional role of telomerase in the cell; not only in its ability to regulate genes and limit replication but also its ability to mobilize dormant stem cells to regenerate cells and tissue, an important regenerative implication. Flores, Ignacio, and Maria A Blasco. FEBS letters 584.17 (2010): 3826-3830, incorporated herein in its entirety by reference.

The ability of TERT to regenerate epithelial proliferation via stem cell activation and WNT and MYC pathways is a key component to this rejuvenation, in addition to the changes in cell gene expression controlled by the telomeres. Choi, Jinkuk et al., PLoS Genetics 4.1 (2008): e10. This regenerative potential was again recently demonstrated in the treatment of myocardial infarction. Bar, Christian et al., Nature Communications 5 (2014). The rejuvenation of telomeres in skin and muscle cells was demonstrated with use of modified RNA to activate the telomerase gene and the aged cell returned to youthful gene expression and function. Ramunas, John et al. The FASEB Journal 29.5 (2015): 1930-193. Fibroblasts thus treated divided forty times in addition to their functional lifespan without observed negative effects. Eventually, cells resumed aging, showing that the effect was transient and that cellular age is elastic.

The genes of this invention can be delivered in one of the modalities known to one of ordinary skill in the art such as a viral, protein, ligand, plasmid, or liposomal delivery system. In one embodiment, the adeno-associated viral (AAV) vector platform is used to insert genes to treat a disorder and are modified for the enhanced delivery to neural tissue. The virus delivers the genes of interest to the subject's cells. In recent years AAV gene therapies have been tested in humans with great success and no evidence of adverse effects. There are numerous clinical trials currently being conducted with AAV gene therapy for many diseases.

The Epigenetic/Telomere Theory of Aging

The telomere theory of aging can be put in one sentence: Cells divide, telomeres shorten, gene expression changes, the cellular repair and recycling process slows down, errors slowly accumulate, and cells ultimately fail.

Telomeres were originally considered to be simple counters of cell division. However, telomeres protect the chromosome from damage and affect the gene expression of all the genes on that chromosome, through a mechanism known as the telomere position effect (TPE). Wright and Shay and a number of other leading scientists have demonstrated how the telomeres affect this gene expression throughout life.

These changes in gene expression in effect reprogram the cell as the telomeres shorten and contribute to the dysfunctional changes associated with aging. This programmed change of gene expression and resulting dysfunction is different than changes in gene expression through DNA methylation and histone acetylation patterns called "epigenetic drift," although they share similarities. Both processes are influenced by genotype, both appear to result in stem cell dysfunction, both occur independently of tissue and, finally, both are linked to disease risk factors. Epigenetic drift likely constitutes a second aging "clock" within the cell and should be the focus of life extension therapies in conjunction with telomere restoration to potentially restore youthful cell function. Dr. Michael Fossel, one of the foremost advocates of the telomere or epigenetic theory of aging, explains that it is not the absolute length of telomeres which control aging, but the level of erosion relative from the time the egg was fertilized. As Fossel explains, "Telomere length is irrelevant, telomere loss is critical." Fossel, Michael B., M. D., Cells, Aging, and Human Disease, Oxford University Press, New York, N.Y. (2004):36, incorporated herein in its entirety by reference. In summary, the rate of telomere shortening appears to depend on the telomeres original length.

People starting out with the longest telomeres experience the fastest rate of telomere shortening and vice versa. This explains how mice, with significantly longer telomeres compared to humans, still have shorter life spans. So, it is the restoration of telomere loss, and restoration of the telomere to its initial length, that is the goal rather than simply extending them as much as possible. This shortening eventually causes the cell to enter senescence; not because the chromosomes are not properly capped, but because the gene expression has altered to the point that the cell ceases to be functional.

The question over whether some older people have enough senescent cells to explain their aged tissue is resolved by the fact that cell senescence is only part of the picture. Gene expression patterns cause older phenotypes to be expressed, and become functionality reduced, in all elderly cells. Coupled with changes in gene expression, senescent cells cause further damage as a significant number of these exhausted cells resist apoptosis (their natural death) and remain in place, sending out damaging signals known as the senescence-associated secretory phenotype (SASP). Senescent cells are a part of the larger picture and, aside from cancer cells, are some of the most dangerous and dysfunctional cells. Senescent cells are incapable of division and are toxic to neighboring cells through the damaging signals via SASP.

A relatively small number of senescent cells create a far greater problem. The area of senolytic agents, substances capable of removing them, has been of considerable interest. The slow division of certain cell populations (neurons, cardiomyocytes and myocytes) that may pose objections to the epigenetic theory of aging are overcome by the support from their dividing neighbors slowly dividing cells require. Each neuron, for example, is surrounded by Glial cells, which do divide and whose telomeres do shorten. The support provided by these glial cells is lost in old age. Moreover, age compromises the blood supply to the brain as the cells of the arteries begin aging due to the gene expression changes caused by telomere erosion. For every non-dividing tissue type, this loss of support from their neighboring dividing cells is consistent with the pathology that we observe in the non-dividing tissues as they age.

In conclusion, telomeres are a primary target of interventions to promote the reversal in gene expression that will mitigate the effects of aging and revert cells to a younger, healthier pattern of expression. Numerous experiments demonstrate that restoring relative telomere length rejuvenates cells and the tissue(s) they comprise, in both animal and human cells tested. Therefore after decades of testing and research it is finally time to develop this as a restorative therapy with the potential to address a myriad of age associated conditions and to potentially extend lifespan considerably.

Follistatin Gene

Growth and differentiation factor-8 (GDF-8), also known as myostatin, is a member of the transforming growth factor-beta (TGF-β.) superfamily of structurally related growth factors, all of which possess important physiological, growth-regulatory, and morphogenetic properties. GDF-8 is a negative regulator of skeletal muscle mass, and there is considerable interest in identifying factors which regulate its biological activity. For example, GDF-8 is highly expressed in the developing and adult skeletal muscle. The GDF-8 null mutation in transgenic mice is characterized by a marked hypertrophy and hyperplasia of the skeletal muscle. Similar increases in skeletal muscle mass are evident in naturally occurring mutations of GDF-8 in cattle.

Of the factors that enhance the formation of muscle and factors that inhibit muscle formation, myostatin is one of the main factors that inhibit muscle growth, but there are related proteins with similar functions. Myostatin and related proteins bind to receptors on the muscle cells and signal the myocyte to stop growing. When the gene for the myostatin protein is mutated and no myostatin is made, this leads to increased muscle formation in animals (Belgian blue cows, Texel sheep and greyhounds) and humans. Thus, if it is possible to prevent myostatin from doing its job, this should enhance muscle formation. This could compensate for the loss of muscle tissue in sarcopenia, muscular dystrophy and other muscular wastage conditions and can be achieved by gene therapy for myostatin inhibition. These antibodies may bind to myostatin and prevent it from reaching the gene switches and turning down the level of expression, thus mitigating the loss of muscle.

Follistatin is a protein that inhibits myostatin, a protein that inhibits muscle growth and thus by increasing the levels of Follistatin, myostatin is inhibited, which will lead to an increase in muscle mass. The Follistatin gene has been delivered to mice and monkeys using an AAV viral vector and the injections resulted in an increase in muscle mass and muscle strength. Similar promising results have been demonstrated in a recent gene therapy for Becker's MD with some excellent results.

The Follistatin gene, as a full-length version, encodes a 344-amino acid preprotein, FS344, differing by a 27-amino acid sequence from its carboxy-shortened version of the 317-amino acid form. Prior to activation, follistatin, like myostatin, undergoes further post-translational modification to lose another 29 amino acids by removal of the signal peptide that results in polypeptides of 315 (FS315), often referred to as the long isoform and 288 (FS288), called the short isoform. Animal studies have shown that the administration of an alternatively spliced FS344 gene in adeno-associated viral (AAV) vector resulted in increases in muscle mass and strength in several species. Rodino-Klapac, L., et al, 39(3) Muscle Nerve: 283-296 (2009), incorporated herein in its entirety by reference. Follistatin was shown to be one of only three proteins that are reduced in amyotrophic lateral sclerosis, along with interleukin-I alpha, and kallikrein-5, when statistically compared to age-matched controls. Lind, A L et al, 11(2) PLoS ONE: 2-17 (2016), incorporated herein in its entirety by reference. The DNA is set forth as SEQ ID NO 3 of U.S. Pat. No. 8,895,309 to Kasper and Mendell, Nov. 25, 2014 and was submitted to the GENBANK as SEQ ID NO 3 of WO2008067480 filed contemporaneously, on Nov. 27, 2007, incorporated herein in their entirety by reference.

Novel Gene Therapy

Disclosed are compositions, methods, and systems of gene therapy for treating or preventing age-related and other disorders. In some embodiments, gene therapy compositions include a therapeutic amount of follistatin and/or hTERT, a viral vector or other suitable delivery mechanism, and/or a pharmaceutically appropriate carrier. In some embodiments, the therapeutic amount is suitable for administration to a human, mouse, rabbit, goat, or other mammal. In some embodiments, methods of treating or preventing an age-related or other disorder include administering a gene therapy composition to a mammalian subject, wherein administering the gene therapy composition lengthens the telomeres of the mammalian subject in one or more tissues.

This inventor has discovered a method to bring the 1999 teachings of Michael West of Geron to their culmination of cellular regeneration, not limited to individual cells in vitro but their regeneration within the human tissue(s) they compose. The administration of Follistatin and hTERT is expected to promote the division of stem cells and prevent their depletion, regenerating the organism the stem cells are a part of. Both genes are available from sources well known to those of ordinary skill in the art. The regeneration of a human being will ultimately prove the concept and culminate decades of work.

The component genes of this invention can be delivered in one of the modalities known to one of ordinary skill in the art such as a viral, protein, ligand, plasmid, or liposomal delivery system. In one embodiment, the adeno-associated viral (AAV) vector platform is used to insert genes to treat a disorder and are modified for the enhanced delivery to neural tissue. The virus delivers the genes of interest to the subject's cells of one or more tissue(s). In recent years, AAV gene therapies have been tested in humans with great success and no evidence of adverse effects. There are numerous clinical trials currently being conducted with AAV gene therapy for many diseases.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification.

DETAILED DESCRIPTION

Figure 1A:
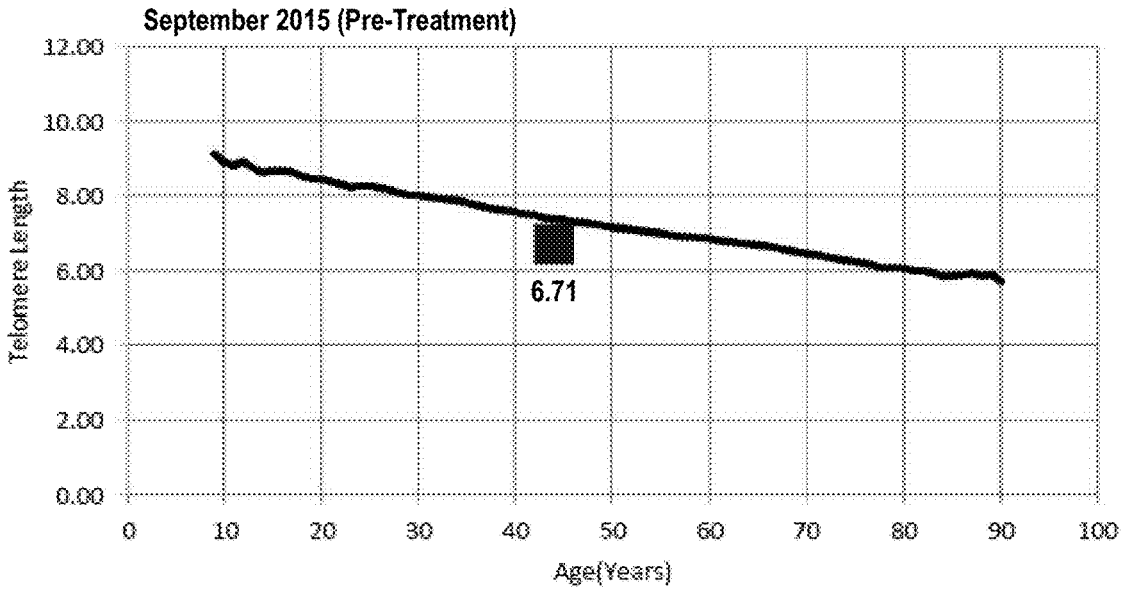
FIGS. 1A through 1E show results of a test in which the hTERT gene was administered in combination with the Follistatin-344 gene to a human subject. The figures illustrate the subject's telomere length and age relative to the average telomere length of a sample population across an age range. The results show that although the subject's pre-treatment telomere length was below average for those of similar age, over time following treatment, the subject's telomere length recovered to average and then exceeded average for those of similar age.
Figure 1B:
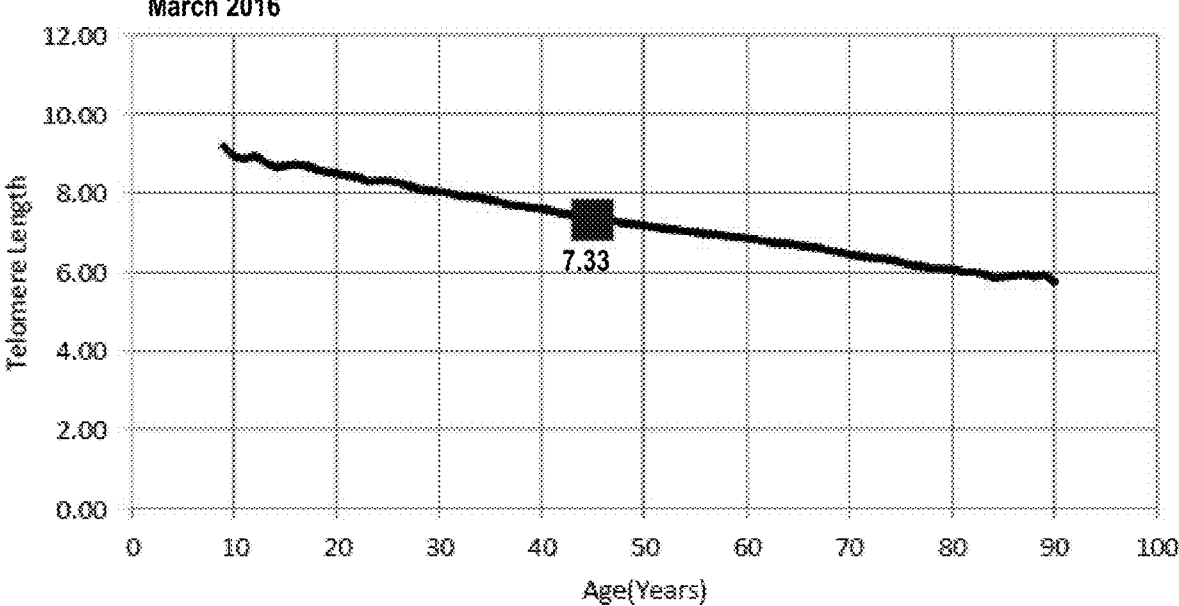
Figure 1C:
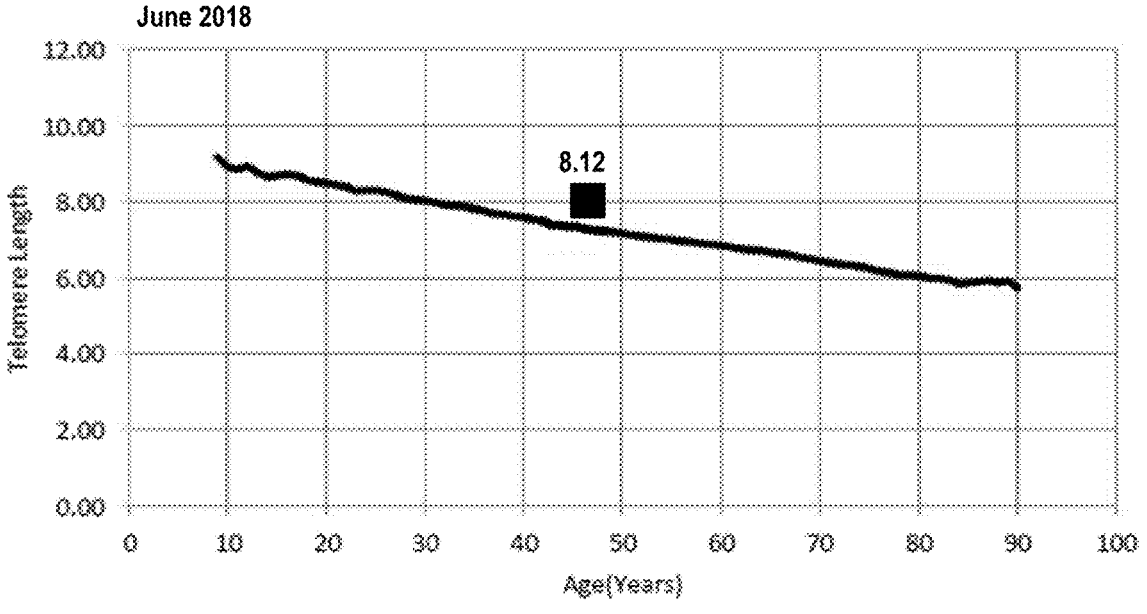
Figure 1D:
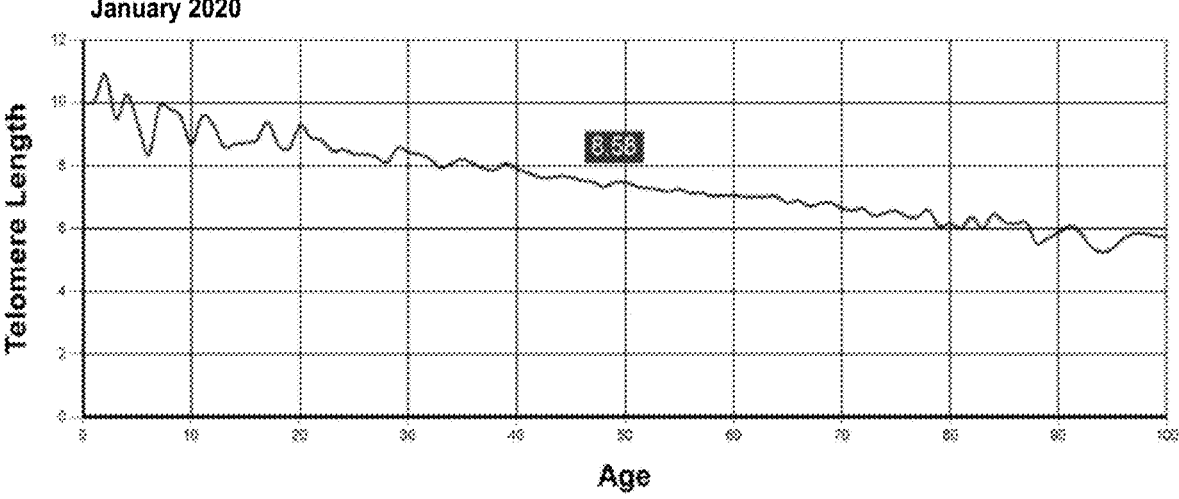

Applicant has discovered a method of treating or preventing age-related disorders in a subject comprising administering to the subject a therapeutically effective amount of a human Telomerase Reverse Transcriptase (hTERT) gene in combination with a Follistatin gene. Follistatin is characterized according to its number of base pairs as Follistatin-344, Follistatin-315, Follistatin-288 or Follistatin-303. In some embodiments, the Follistatin-344 gene is preferred. Specifically, the subject may be any mammal such as an ovine (sheep), bovine (cattle), porcine (hogs or pigs), murine (rats or mice) or primate (apes, monkeys, and humans) mammal; most specifically a human.

The hTERT and Follistatin-344 genes may be administered in a delivery method selected from the group consisting of an adeno-associated viral vector, protein, ligand, plasmid, liposomal or other applicable delivery method and may be administered in a number of intravenous, subcutaneous, or intramuscular injections. In some embodiments, the injections may be administered between 1 and 6 times (or more) for both the hTERT and the Follistatin-344 gene. In some embodiments, the injections may be administered between 2 and 7 times (or more) for both the hTERT and the Follistatin-344 gene. In some embodiments, such injections and/or other modes of administration may be administered to the subject several times. For example, the gene therapy treatments described herein may be administered according to a regular schedule (e.g., annually, semi-annually, monthly, semi-monthly, weekly, or other appropriate schedule). In some embodiments, a higher proportion of treatment cycles are administered during one or more initial phases of treatment, followed by one or more less frequent "maintenance" treatment cycles. Those of skill in the art, in light of this disclosure, are able to customize treatment regimens for particular subject needs.

In some embodiments, the hTERT gene may be administered in a dosage between about 1×10E14 to 5×10E15 as a lower endpoint and up to about 5×10E17 units. In some embodiments, the Follistatin gene may be administered in a dosage between 5×10E14 units and 5×10E16 units. In some embodiments, the Follistatin-344 gene may be administered in a dosage between 5×10E14 units and 5×10E16 units. In some embodiments, the hTERT gene may be administered in a dosage between 5×10E14 and 5×10E17 units and the Follistatin-344 gene may be administered in a dosage between 5×10E14 units and 5×10E16 units. In some embodiments, the hTERT gene is administered by intravenous and/or subcutaneous injection in an adeno-associated viral vector (AAV-hTERT) and the Follistatin-344 gene is administered in one or more (e.g., about five (5)) intramuscular injections of adeno-associated viral vector (AAV-FS344). Unless specified otherwise, the therapy dosage units described herein are expressed as physical titer numbers equivalent to viral genomes per ml (vg/ml), which may be determined, for example, by qPCR of purified vector particles.

The hTERT and Follistatin-344 genes may be administered in a vector selected from a plasmid, phage, virus, bacterial artificial chromosome (BAC), yeast artificial chromosome (YAC). In some embodiments, the virus is an adeno-associated viral (AAV) vector, a herpesvirus vector, or a baculovirus vector.

Disorders treated by this invention may be one related to age such as a wasting disorder, a metabolic disorder, or a disorder of the connective tissue. Wasting disorders effectively treated include those selected from the group of cachexia, anorexia, sarcopenia, skin atrophy, and muscle wasting disorders. Metabolic disorders effectively treated include those selected from the group consisting of obesity, metabolic syndrome, syndrome X, renal disease, hyperglycemia, anorexia, and type II diabetes. Disorders of the connective tissue may be those of bone, blood or cartilage including osteoarthritis, osteoporosis, and cardiovascular, cardiopulmonary, and/or pulmonary disorders such as hypertension, hyperlipidemia, hypercholesterolemia, hyperhomocysteinemia, atherosclerosis, arteriosclerosis, myocardial infarction, congestive heart failure, peripheral vascular disease, pulmonary emphysema, pulmonary fibrosis, stroke, and anemia.

Age-related disorders may be neurogenerative and include Alzheimer's disease, cataracts, age-related hearing loss, dementia, chronic traumatic encephalopathy (CTE), brain atrophy, amyotrophic lateral sclerosis (ALS), Parkinson's disease, Gillian-Barre syndrome, peripheral neuropathy, macular degeneration, Creutzfeldt-Jakob disease, dementia associated with trauma, frontotemporal dementia, spinal muscular atrophy, and Friedreich's ataxia, all of which may be prevented or treated by the disclosed methods.

The disclosed methods may be used to increase strength and muscle tissue growth in a subject by administering to a subject a therapeutically effective amount of a human Telomerase Reverse Transcriptase (hTERT) gene in combination with a Follistatin-344 gene, in a number of intravenous, subcutaneous or intramuscular injections, for example between 1 and 6. Clinical studies comparing this administration to the administration of a placebo show a two at least two-fold greater than the muscle tissue growth of a corresponding subject treated with placebo.

The hTERT and Follistatin-344 genes may be administered in a vector selected from a plasmid, phage, bacterial artificial chromosome (BAC), yeast artificial chromosome (YAC), or virus such as an adeno-associated viral (AAV) vector, a herpesvirus vector, or a baculovirus vector. In some embodiments, the genes include SEQ ID NO:1 for the hTERT DNA and SEQ ID NO:2, for the Follistatin-344 RNA. In some embodiments, the administered genes need not have 100% sequence identity with SEQ ID NO:1 and SEQ ID NO:2, but have at least 80% sequence identity, or at least 85% sequence identity, or at least 90% sequence identity, or at least 95% sequence identity, or at least 97.5% sequence identity, or at least 99% sequence identity with SEQ ID NO:1, or a fragment thereof, and SEQ ID NO:2, or a fragment thereof, respectively.

The therapy components may be administered with a vector selected from a plasmid, phage, bacterial artificial chromosome (BAC), yeast artificial chromosome (YAC) or viral particle such as an adeno-associated viral (AAV) vector, a herpesvirus vector, or a baculovirus vector.

The administrable composition is therapeutically effective for increasing muscle tissue mass and for treating or preventing age-related disorders such as a wasting disorder such as cachexia and anorexia; a metabolic disorder such as obesity and type II diabetes; a cardiovascular disorder such as atherosclerosis, arteriosclerosis, myocardial infarction, congestive heart failure, peripheral vascular disease and stroke; a disorder of the bones and connective tissue such as osteoarthritis, osteoporosis, and fibromyalgia. The composition treats or prevents an age-related neurodegenerative disorder such as Alzheimer's disease, cataracts, age-related hearing loss, dementia, chronic traumatic encephalopathy (CTE), brain atrophy, amyotrophic lateral sclerosis (ALS), Parkinson's disease, Gillian-Barre syndrome, peripheral neuropathy, macular degeneration, Creutzfeldt-Jakob disease, dementia associated with trauma, frontotemporal dementia, spinal muscular atrophy, and Friedreich's ataxia.

Increased Telomere Length

As described in additional detail in the Examples section, methods described herein may be utilized to slow the decrease in telomere length in a subject. Methods described herein may be utilized to stop the decrease in telomere length in a subject. Methods described herein may be utilized to increase telomere length in a subject. The subject may be a human. Telomere length may be increased in one or more cell types in the subject. In some embodiments, telomere length may be determined by testing white blood cells, for example.

In some embodiments, the subject's telomeres do not decrease in length (or even increase in length) in the first 3-12 months following initial treatment. In some embodiments, the subject's telomeres do not decrease in length (or even increase in length) in the first 2, 3, 4, 5, 6, 7, 8, 9, or 10 years following initial treatment.

In some embodiments, the subject's telomeres are increased in length by up to about 1%, up to about 2.5%, up to about 5%, up to about 10%, up to about 15%, or up to about 20%, in the first six months following initial treatment. In some embodiments, the subject's telomeres are increased in length by up to about 1%, up to about 2.5%, up to about 5%, up to about 10%, up to about 15%, up to about 20%, up to about 25%, or up to about 30% in the first 36 months following initial treatment. In some embodiments, the subject's telomeres are increased in length by up to about 1%, up to about 2.5%, up to about 5%, up to about 10%, up to about 15%, up to about 20%, up to about 25%, up to about 30%, up to about 35%, up to about 40%, up to about 45%, in the first 5 to 6 years following initial treatment.

Additional Terms & Definitions

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may also include properties and/or features (e.g., ingredients, components, members, elements, parts, and/or portions) described in one or more separate embodiments and are not necessarily limited strictly to the features expressly described for that particular embodiment. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

EXAMPLES

Example 1: Increased Telomere Length in a Human Subject

The AAV therapy regimen described herein, comprising administration of the hTERT gene administered in combination with administration of the Follistatin-344 gene, was tested on a female human subject. Pre-treatment measurements were acquired on Sep. 15, 2015. The subject was 44 years old at the time pre-treatment measurements were acquired. The pre-treatment measurements included average telomere length, telomere length percentile relative to others of patient's age and population, and associated age (i.e., the age that typically corresponds to the measured telomere length in the population at large).

Two treatment cycles were given. The first cycle was administered on Sep. 16, 2015 and was followed by two post-treatment measurements. The second cycle was administered on Sep. 24, 2020 and was followed by one post-treatment measurement. Each treatment was implemented by administering 1×10e15 units of AAV-FS344 via intramuscular injection and 3×10e15 units of AAV-hTERT divided between separate subcutaneous and intravenous injections. The results of the pre-treatment and post-treatment measurements for telomere length are illustrated in Table 1, below.

The subject's telomere length was assessed and provided as a "telomere score" equal to the length of the measured telomeres in units of kilobases (kb). Analysis of the subject's telomere length/score was conducted by SpectraCell Laboratories of Houston, Tex. The telomere score is a calculation of the subject telomere length derived from nucleated white blood cells obtained from whole blood. The higher the telomere score, the "younger" the cells.

As can be seen in Table 1, administration of the AAV dual-gene therapy regimen improved the telomere length of the tested cells. An increase in telomere length of approximately 10% (relative to pre-treatment measurement) was seen in the first six months of treatment. Another increase of approximately 10% was seen over the next two years. As of July 2021, the telomere score had increased to 8.94, or approximately 33% above the initial pre-treatment measurement of 6.71.

TABLE 1

Telomere Scores & Percentiles of Test Subject over Time

|  | Sep. 17, 2015 | Mar. 18, 2016 | Jun. 16, 2018 | Jan. 18, 2020 | Jul. 13, 2021 |
|---|---|---|---|---|---|
| Telomere length (kb) | 6.71 | 7.33 | 8.12 | 8.58 | 8.94 |
| Percentile | 30 | 51 | 72 | 82 | 89 |

As further shown in Table 1, the subject's telomere length was also compared to others of the same age and reported as a percentile. In the initial, pre-treatment measurement, the subject's telomere length was at the $30^{th}$ percentile. Six months after the first treatment, the subject's telomere length had improved to the $51^{st}$ percentile (i.e., approximately average relative to others of the same age). The subject's telomere length relative to others of the same age continued to improve. As of the Jul. 13, 2021 measurement, the subject's telomere length was in the $89^{th}$ percentile.

Figure 1E:
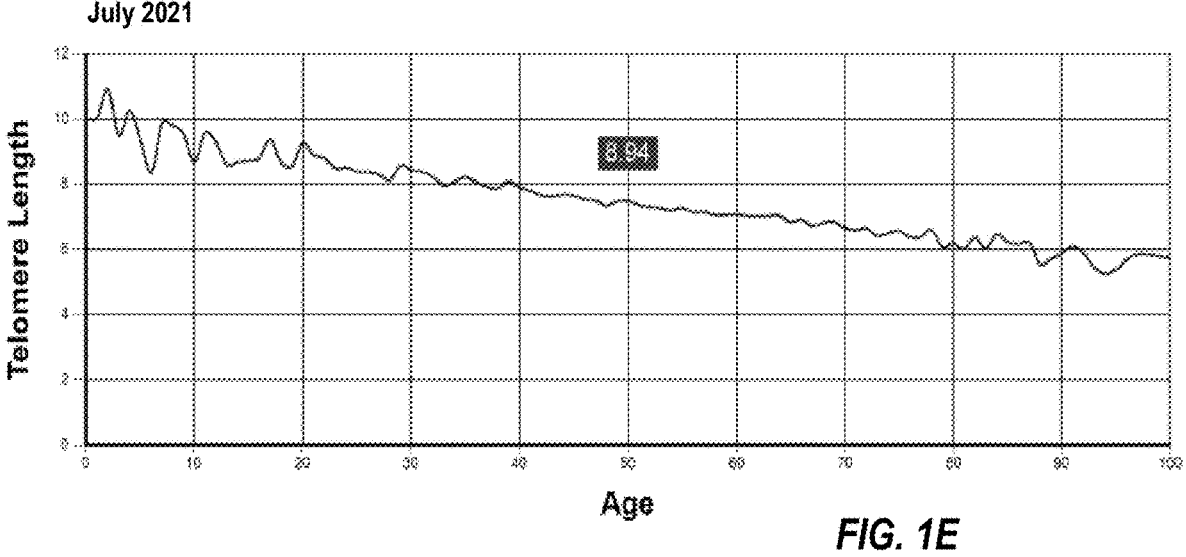

FIGS. 1A through 1E correspond to Table 1 and show the subject's telomere length and age relative to the average telomere length of a sample population across an age range. As shown, the subject's pre-treatment telomere length was below average for those of similar age. However, over time following treatment, the subject's telomere length recovered to average and then exceeded average for those of similar age. As shown in FIG. 1E, as of the Jul. 13, 2021 measurement, at the $89^{th}$ percentile, the subject's measured telomere length matched the average for an individual in his/her teenage years or early twenties, even though the subject was 50 years old when the last measurement was taken.

Figure 2A:
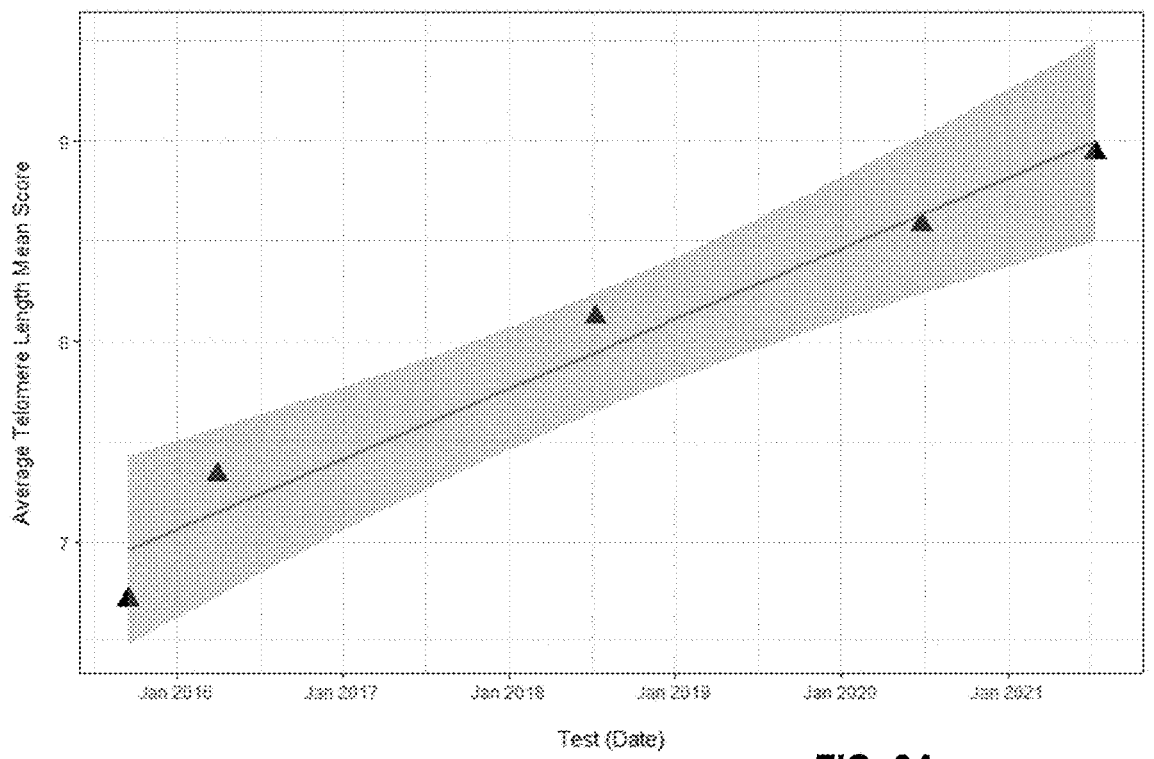
FIGS. 2A through 2C show regression analyses of based on the data resulting from the test of FIGS. 1A through 1E. The regression analyses show that the subject's telomere length significantly increased during the post-treatment period (p=0.003) at a rate of about 0.35 kb per year, that the subject's percentile relative to others of the same age significantly increased during the post-treatment period (p=0.010) at a rate of about 9.1 percent per year, and that the subject's associated age significantly decreased during the post-treatment period (p=0.018) at a rate of about 5.3 years per year.

FIG. 2A illustrates the subject's measured telomere length over time showing the associated regression line. The related statistical analysis is shown in Table 2A.

TABLE 2A

Regression Analysis of Telomere Length Data

|  | Estimate | Std. Err. | T value | P value |
|---|---|---|---|---|
| Intercept | 6.958 | 0.148 | 46.942 | <0.001 |
| Time | 0.350 | 0.041 | 8.524 | 0.003 |

The analysis showed that the subject's telomere length significantly increased during the post-treatment period (p=0.003) at a rate of about 0.35 kb per year.

Figure 2B:
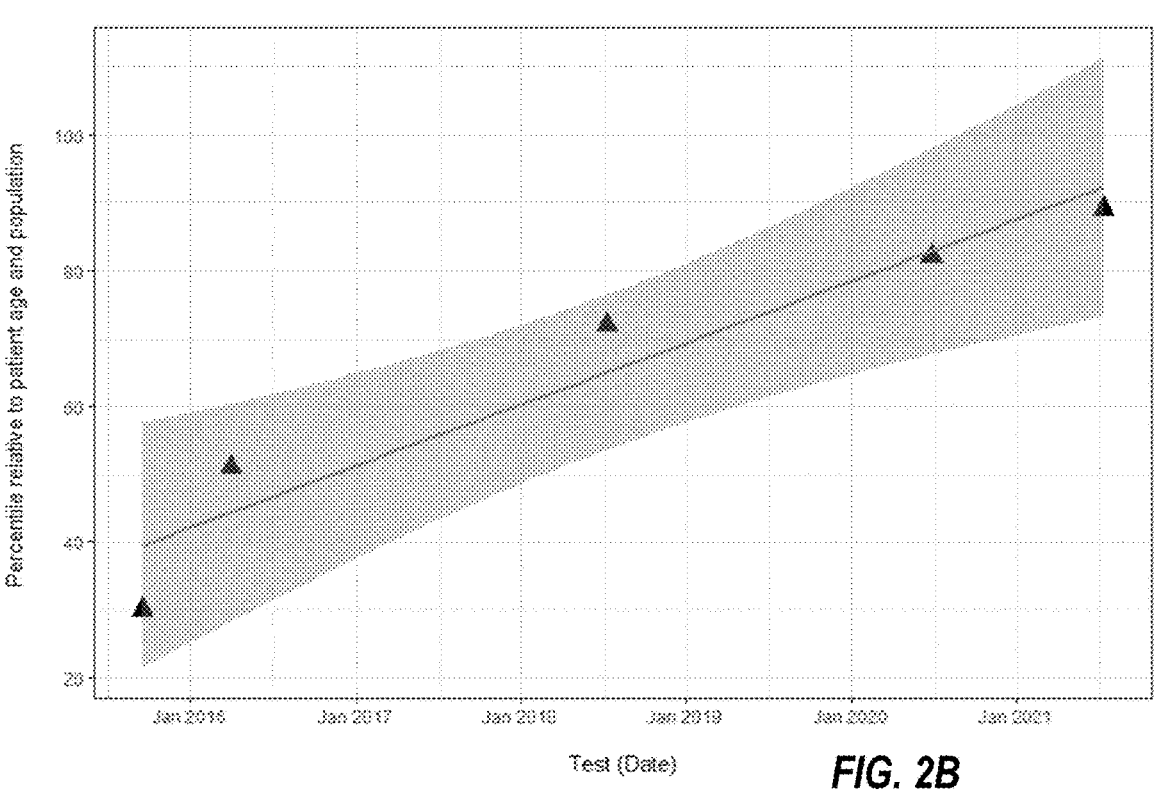

FIG. 2B illustrates the subject's telomere percentile over time, showing the associated regression line. The related statistical analysis is shown in Table 2B.

TABLE 2B

Regression Analysis of Telomere Percentile Data

|  | Estimate | Std. Err. | T value | P value |
|---|---|---|---|---|
| Intercept | 39.475 | 5.685 | 6.943 | 0.006 |
| Time | 9.069 | 1.577 | 5.752 | 0.010 |

The analysis shows that the subject's percentile relative to others of the same age significantly increased during the post-treatment period (p=0.010) at a rate of about 9.1 percent per year.

Figure 2C:
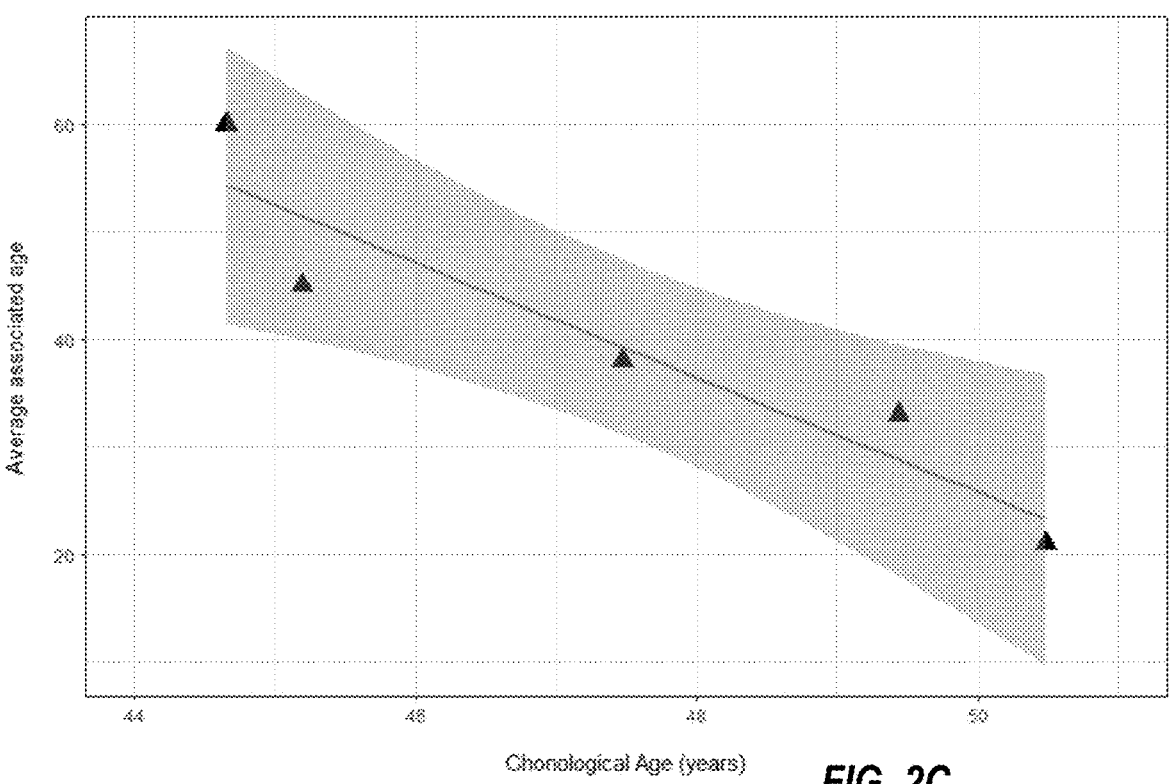

FIG. 2C compares the subject's "associated age" to the subject's chronological (actual) age, showing the associated regression line. The "associated age" is the age at which the test population's average telomere length matches the subject's measured telomere length. The related statistical analysis is shown in Table 2C.

TABLE 2C

Regression Analysis of Associated Age Data

|  | Estimate | Std. Err. | T value | P value |
|---|---|---|---|---|
| Intercept | 292.097 | 53.162 | 5.494 | 0.012 |
| Time | −5.326 | 1.119 | −4.759 | 0.018 |

The analysis shows that the subject's associated age significantly decreased during the post-treatment period (p=0.018) at a rate of about 5.3 years per year.

Example 2: Increased Muscle Mass in a Human Subject

Figure 3A:
FIGS. 3A and 3B are MRI images of the treated subject's thigh, respectively, prior to and after effects of the gene therapy treatment were expected, the later image showing more musculature and less intermuscular fat relative to the initial image.
Figure 3B:

The same female subject of Example 1 also underwent Magnetic Resonance Imaging (MM) at two separate time points to monitor changes to thigh musculature. The first set of MRI images were obtained on Oct. 29, 2015, only a few weeks after the first treatment cycle was administered. FIG. 3A shows an MM image from the first set. The second set of MRI images were obtained on Aug. 6, 2016, nearly a year following the first treatment cycle. FIG. 3B shows an MM image from the second set. The later image of FIG. 3B showed more muscle and less intermuscular fat.

Example 3: Improved Blood Glucose Measures in a Human Subject

The same female subject of Examples 1 and 2 also underwent blood testing before and after the second treatment cycle was administered. The subject provided blood on Sep. 15, 2020 (prior to the second treatment cycle), and the fasting glucose level was measured at 92 mg/dL. The subject then provided blood on Feb. 2, 2021 (after the second treatment cycle), and the fasting glucose level was measured at 83 mg/dL, a beneficial reduction from the previous measurement.

---

The invention claimed is:

1. A method comprising:
   administering to a human a therapeutically effective amount of a human Telomerase Reverse Transcriptase (hTERT) gene in combination with a Follistatin-344 gene,
   wherein the hTERT gene is administered via intramuscular injection and the Follistatin-344 gene is administered via subcutaneous injection and intravenous injection,
   wherein the method provides one or more of
      (i) increasing telomere length in at least some cells of the human,
      (ii) decreasing muscle loss, maintaining muscle mass, or increasing muscle mass in the human, or
      (iii) improving blood glucose levels in the human.

2. The method of claim 1, wherein the hTERT and Follistatin-344 genes are administered in a vector selected from a plasmid, phage, bacterial artificial chromosome (BAC), yeast artificial chromosome (YAC), or virus.

3. The method of claim 2 wherein the vector is a virus selected from an adeno-associated viral (AAV) vector, a herpesvirus vector, or a baculovirus vector.

4. The method of claim 3, wherein the vector is an AAV vector.

5. The method of claim 1, wherein the method increases telomere length in white blood cells.

6. A method comprising:
   administering to a human a therapeutically effective amount of a human Telomerase Reverse Transcriptase (hTERT) gene in combination with a Follistatin-344 gene,
   wherein the hTERT gene is administered via intramuscular injection and the Follistatin-344 gene is administered via subcutaneous injection and intravenous injection,
   wherein the hTERT and Follistatin-344 genes are administered using an adeno-associated viral (AAV) vector, and wherein the method increases telomere length in at least some cells of the human.

7. The method of claim 6, wherein the method increases telomere length in white blood cells.

8. The method of claim 6, wherein the method further provides one or more of: decreased muscle loss, maintained muscle mass, or increased muscle mass in the human.

9. The method of claim 6, wherein the method further improves blood glucose levels in the human.

10. A method comprising:
   administering to a human a therapeutically effective amount of
   (i) a human Telomerase Reverse Transcriptase (hTERT) gene via intramuscular injection, and
   (ii) a Follistatin-344 gene via subcutaneous injection, intravenous injection, or both,
   wherein the method provides one or more of
      (i) increasing telomere length in at least some cells of the human,
      (ii) decreasing muscle loss, maintaining muscle mass, or increasing muscle mass in the human, or
      (iii) improving blood glucose levels in the human.

11. The method of claim 10, wherein the hTERT and Follistatin-344 genes are administered in a vector selected from a plasmid, phage, bacterial artificial chromosome (BAC), yeast artificial chromosome (YAC), or virus.

12. The method of claim 11 wherein the vector is a virus selected from an adeno-associated viral (AAV) vector, a herpesvirus vector, or a baculovirus vector.

13. The method of claim 12, wherein the vector is an AAV vector.

14. The method of claim 10, wherein the method increases telomere length in white blood cells.

* * * * *

SEQUENCE LISTING

<160> NUMBER OF SEQ ID NOS: 2

<210> SEQ ID NO 1
<211> LENGTH: 1035
<212> TYPE: DNA
<213> ORGANISM: Homo sapiens

<400> SEQUENCE: 1

```
atggtccgcg cgaggcacca gccgggtggg ctttgcctcc tgctgctgct gctctgccag      60
ttcatggagg accgcagtgc ccaggctggg aactgctggc tccgtcaagc gaagaacggc     120
cgctgccagg tcctgtacaa gaccgaactg agcaaggagg agtgctgcag caccggccgg     180
ctgagcacct cgtggaccga ggaggacgtg aatgacaaca cactcttcaa gtggatgatt     240
ttcaacgggg gcgcccccaa ctgcatcccc tgtaaagaaa cgtgtgagaa cgtggactgt     300
ggacctggga aaaaatgccg aatgaacaag aagaacaaac cccgctgcgt ctgcgccccg     360
gattgttcca acatcacctg gaagggtcca gtctgcgggc tggatgggaa aacctaccgc     420
aatgaatgtg cactcctaaa ggcaagatgt aaagagcagc cagaactgga agtccagtac     480
caaggcagat gtaaaaagac ttgtcgggat gttttctgtc caggcagctc cacatgtgtg     540
gtggaccaga ccaataatgc ctactgtgtg acctgtaatc ggatttgccc agagcctgct     600
tcctctgagc aatatctctg tgggaatgat ggagtcacct actccagtgc ctgccacctg     660
agaaaggcta cctgcctgct gggcagatct attggattag cctatgaggg aaagtgtatc     720
aaagcaaagt cctgtgaaga tatccagtgc actggtggga aaaaatgttt atgggatttc     780
aaggttggga gaggccggtg ttccctctgt gatgagctgt gccctgacag taagtcggat     840
accttgttct gtgccagtga caatgccact tatgccagcg agtgtgccat gaaggaagct     900
gcctgctcct caggtgtgct actggaagta aagcactccg gatcttgcaa ctccatttcg     960
gaagacaccg aggaagagga ggaagatgaa gaccaggact acagctttcc tatatcttct    1020
attctagagt ggtaa                                                     1035
```

<210> SEQ ID NO 2
<211> LENGTH: 817
<212> TYPE: RNA
<213> ORGANISM: Homo sapiens

<400> SEQUENCE: 2

```
aggccgcgcg aggcaccagc cggggggcgc cccgcgcgcg ccgccagcag gaggaccgca      60
ggcccaggcg ggaacgcggc ccgcaagcga agaacggccg cgccaggccg acaagaccga     120
acgagcaagg aggaggcgca gcaccggccg gcgagcaccc gggaccgagg aggacggaag     180
acaacacacc caagggagac aacggggcg cccccaacgc accccgaaag aaacgggaga     240
```

-continued

```
acgggacggg accgggaaaa aagccgaaga acaagaagaa caaaccccgc gcgcgcgccc     300
cggagccaac acaccggaag ggccagcgcg ggcggaggga aaaccaccgc aagaaggcac     360
ccaaaggcaa gagaaagagc agccagaacg gaagccagac caaggcagag aaaaagacgc     420
gggagcgcca ggcagcccac aggggggacc agaccaaaag ccacgggacc gaacggagcc     480
cagagccgcc ccgagcaaac cggggaagag gagcaccacc caggccgcca ccgagaaagg     540
caccgccgcg ggcagacagg aagccagagg gaaaggacaa agcaaagccg gaagaaccag     600
gcacggggga aaaaagaggg acaagggggga gaggccgggc cccggagagc ggcccgacag    660
aagcggauau ccgcggccag gacaagccac agccagcgag ggccagaagg aagcgccgcc     720
ccaggggcac ggaagaaagc acccggacgc aacccacgga agacaccgag gaagaggagg     780
aagagaagac caggacacag cccaaccaca gagggaa                             817
```